United States Patent [19]

Martinez

[11] Patent Number: 4,955,375
[45] Date of Patent: Sep. 11, 1990

[54] ENDOTRACHEAL TUBE WITH CHANNEL FOR DELIVERING DRUGS

[76] Inventor: Ricardo Martinez, 21 Needleridge Ct., San Mateo, Calif. 94402

[21] Appl. No.: 300,968

[22] Filed: Jan. 23, 1989

[51] Int. Cl.$^5$ .............................................. A61M 16/00
[52] U.S. Cl. .............................. 128/207.15; 604/280; 604/264; 604/43; 128/207.14
[58] Field of Search ...................... 128/207.14, 207.15, 128/200.26, 200.18, 200.21; 604/43, 27, 39, 40, 128, 280, 264

[56] References Cited

U.S. PATENT DOCUMENTS

| | | | |
|---|---|---|---|
| 3,593,713 | 7/1971 | Bogoff et al. | 604/280 |
| 4,150,676 | 4/1974 | Jackson . | |
| 4,369,789 | 1/1983 | LaVeen et al. | 604/96 |
| 4,405,313 | 9/1983 | Sisley et al. | 604/43 |
| 4,468,216 | 8/1984 | Muto | 604/43 |
| 4,637,389 | 1/1987 | Heyden | 128/207.15 |
| 4,674,495 | 6/1987 | Orr | 128/207.14 |
| 4,705,501 | 11/1987 | Wigness et al. | 604/43 |
| 4,738,666 | 4/1988 | Fuqua | 604/280 |
| 4,821,714 | 4/1989 | Smelser | 128/207.14 |
| 4,881,542 | 11/1989 | Schmidt et al. | 128/207.14 |
| 4,892,095 | 1/1990 | Nakhgevany | 128/207.14 |

Primary Examiner—Stephen C. Pellegrino
Assistant Examiner—Mark O. Polutta
Attorney, Agent, or Firm—Irell & Manella

[57] ABSTRACT

An endotracheal tube having a first lumen for ventilation, a second lumen having an elastic, collapsible wall attached to an inner wall of the tube, and optionally a third lumen for supplying an inflatable balloon at a distal end of the tube. The second lumen includes a port for applying medications thereto, and a distal end for expelling such medications at the distal end of the tube. The wall of the second lumen is connected at two line joints to the inner wall of the tube, and includes a flared distal end portion which is tacked down for preventing maintained inflation. The second lumen wall thus forms a boundary between the first lumen and the second lumen, and allows transmission of pressure from the former to the latter. When the tube is inserted into a patient, medication can be applied through the port of the second lumen. Once the medication enters the lumen, pressure within the first lumen collapses the second lumen wall from the proximal end towards the distal end, thus propelling the medication towards the flared portion. The second lumen wall is preferably elastic, such that the elasticity alone is sufficient to force the medication within the second lumen distally. As the medication is forced out of the flared distal end, it is atomized, and thus in condition for application to the bronchi. The tube may also be used for cardiac or other applications.

15 Claims, 2 Drawing Sheets

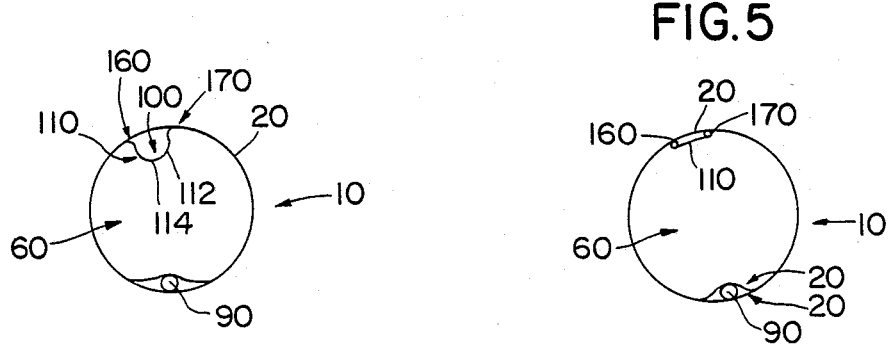
FIG. 2
FIG. 5
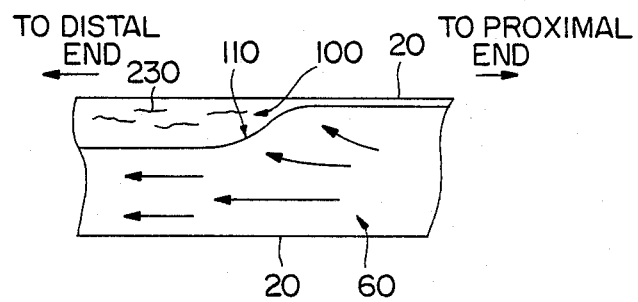
FIG. 4
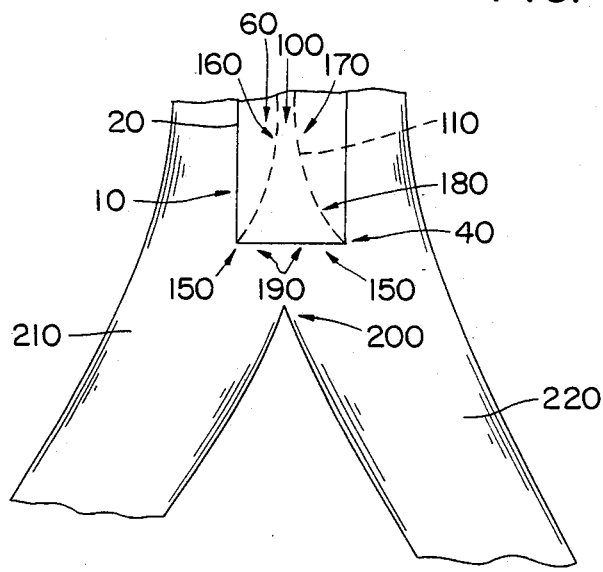
FIG. 3

ENDOTRACHEAL TUBE WITH CHANNEL FOR DELIVERING DRUGS

BACKGROUND OF THE INVENTION

Many lifesaving medications are now known to be absorbed into the central circulation after introduction into the airways via an endotracheal tube, such as in the design of Jackson as described in U.S. Pat. No. 4,150,676 dated Apr. 24, 1979. While this is well known, the logistics of actually introducing the medication through the endotracheal tube are complicated. Resuscitation procedures must stop, the ventilation equipment dismantled, and the medication injected into the open airway. Ongoing cardiopulmonary resuscitation (CPR) must stop for this prolonged period. After introduction of the medication, increased intrathoracic pressures from CPR create an atomized spray of secretions and medication. In today's environment, a device that allows simplified introduction of medications into the airways and decreases the health hazards to medical personnel would have tremendous demand in the prehospital environment, emergency department, and critical care areas. Having this tube in place also allows early introduction of medications into the central circulation prior to placement of venous access.

Therefore, it is an object of this invention to provide an apparatus for delivering liquids to a treatment site without the removal of medical apparatus already in place.

It is a further object of this invention to provide such an apparatus which accommodates the application of atomized liquids to a patient through the use of a new type of catheter.

Other objects and uses will more fully appear in the course of the following discussion.

SUMMARY OF THE INVENTION

The present invention comprises an endotracheal tube having a primary lumen for the supplying of ventilation to the bronchi of a patient, and a second lumen attached to the inside of the first lumen for accommodating the application of medications to the patient even while the tube is in use for ventilation, without removing the ventilating equipment. The second lumen is formed by a flexible elastic wall joined to the main wall of the tube at two sealed line joints. When no liquid is present within the second lumen, the wall thereof collapses flush against the main wall of the tube. When medication is introduced into the second lumen, pressure due to ventilating air or other material present within the first lumen compresses the second lumen wall, forcing the medication from the proximal end of the second lumen towards the distal end thereof. The elasticity of the second lumen wall assists in this compression.

The distal end of the second lumen includes a flared portion tacked down to the main wall by adhesive or the like at several points, such that as the medication is propelled out of the second lumen and into the patient, it is expanded and atomized.

A balloon may be attached in a conventional manner at the distal end of the first lumen, and a third lumen is then included within the main wall, and an air pitot is coupled to the third lumen for inflating the balloon.

BRIEF DESCRIPTION OF THE DRAWINGS

FIG. 2 is a cross-sectional view taken along line 2—2 of FIG. 1.

FIG. 3 is a view of the catheter of the invention in use in a patient.

FIG. 4 is a sectional side view of a portion of the catheter of FIG. 1 when in use.

FIG. 5 is a cross-sectional view similar to that of FIG. 2.

DESCRIPTION OF THE PREFERRED EMBODIMENTS

Figure 1:
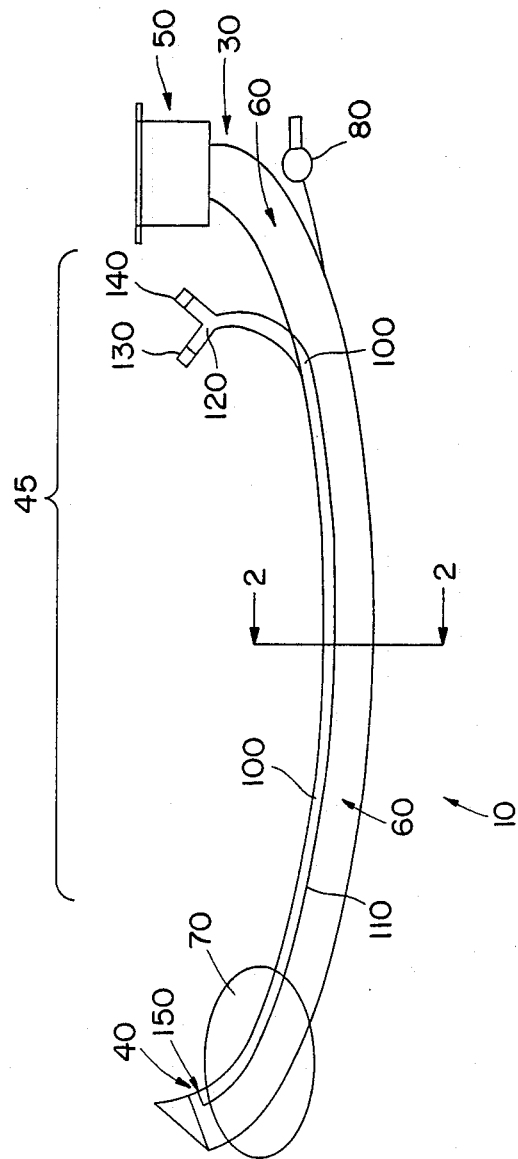
FIG. 1 shows a side view of a catheter incorporating a preferred embodiment of the invention.

Referring to FIGS. 1 and 2, the present invention comprises a catheter or endotracheal tube 10 having a wall 20, a proximal end 30, and a distal end 40. The proximal end 30 may include a coupling device 50 for attachment for ventilating equipment or other medical equipment as desired. A central body 45 is defined between the proximal end 30 and the distal end 40.

The wall 20 defines a first lumen 60 and a second lumen 100 having a distensible, collapsible, flexible wall 110. The lumen 100 is coupled near the distal end 30 of the tube 10 to a y-shaped port 120. The port 120 preferably includes a first tip 130 which is compatible with syringe tips, and a second tip 140 having a covering made of rubber or other soft material in a standard configuration, for being punctured by a needle for the introduction of drugs or the like into the second lumen 100.

The lumen 100 also includes a distal end 150 which is adjacent the distal end 40 of the tube 10. The wall 110 of the lumen 100 is connected in a sealed fashion to the wall 20 of the tube 10 at two line joints 160 and 170. The line joints 160 and 170 may be heat-weld, adhesive, or other conventional means for affixing plastics or other flexible, liquid-impervious materials such as the materials from which the walls 20 and 110 are formed. Thus, as shown in FIG. 2, the wall 110 includes a first side 112 forming at least a part of a boundary for the second lumen 100, and a second side 114 forming a part of a boundary for the first lumen 60. This ensures that pressure within the first lumen 60 is transmitted by the wall 110 to any material which may be present in the second lumen 100.

As shown in FIG. 3, the wall 110 includes a flared portion 180 which is tacked at distal end 150 to the distal end 40 of the tube 10 by means of spot tacks, adhesive or welds 190.

A distal balloon or balloon cuff 70 may be included in a conventional manner as shown in FIG. 1, and is preferably supplied with air under pressure for inflation of the balloon cuff 70 via a third lumen 90 by means of an air pitot 80.

When the tube 10 is in place within a patient, such as immediately above the carina 200 between the left bronchus 210 and the right bronchus 220 as depicted in FIG. 3, ventilation is supplied as normal through the lumen 60. Should it become necessary to provide medication to the patient, it is not necessary to dismantle ventilation equipment; rather, such medication may be supplied through the tips 130 and 140 of the port 120 in liquid form, such as the liquid 230 shown in FIG. 4. Once the liquid 230 enters the lumen 100, further application of pressurized fluid (such as ventilation) through the lumen 60 will cause the wall 110 to collapse flat against the wall 120 at any point where there is no liquid within the lumen 100. This is depicted by the arrows in FIG. 4, which compress the wall 110 from the proximal end 30 towards the distal end 40.

Thus, once the liquid 230 enters the lumen 100, the pressure within the lumen 60 forcibly propels the liquid within the lumen 100 towards the distal end 150, due to the transmission of pressure from the first lumen 60 through the wall 110 to the second lumen 100. As the liquid reaches the flared portion 180 shown in FIG. 3, it rapidly increases in volume, and is expelled past the spot tacks 190, such that it is atomized or sprayed into the bronchi 210 and 220 and thence enters the lungs. The lumen 100 therefore acts as a channel for the delivery of drugs—such as lidocaine, atropine, epinephrine, or the like—to the patient.

In the preferred embodiment, the wall 110 is of an elastic material, such that it resists the increased volume configuration taken on when liquid enters the lumen 100, and assists the pressure within the first lumen 60 in propelling the liquid towards the distal end 150. The elasticity of the wall 110 preferably maintains the wall 110 flush against the wall 20 when no liquid is present in the lumen 100, as shown in FIG. 5. Thus, in the preferred embodiment, the elasticity of the wall 110 is sufficient to force the fluid within the second lumen 100 towards the distal end 40, without the need for pressure due to pressure of the fluid within the first lumen for forcing the fluid or liquid 230 (see FIG. 4) distally. Given both elasticity of the wall 110 and pressurized fluid within the lumen 60, there will be a cumulative effect of force on the liquid 230.

The spot tacks 190 assist in preventing the distal end 150 from maintaining an inflated shape as the liquid is propelled out of the distal end 150.

Similar configurations may be made for other applications; for instance, cardiac catheters can be adapted as described above such that medication may be supplied directly to the heart without removing the catheter or disabling it for use with such medication.

A distinct advantage realized by the present invention, due to the collapsibility and elasticity of the wall 110 and the separate proximal injection port, sprayback of the liquid medication does not occur, which is a problem with present devices, wherein sprayback occurs due to, for instance, CPR pressure or other pressure within the body.

Other embodiments and modifications may be made on the foregoing without departing from the spirit and scope of the invention.

What is claimed is:

1. A catheter, comprising:

a first tube defining a first lumen;

a proximal end;

a distal end;

a first wall of a distensible material attached in a sealed fashion to said first tube within said first lumen between said proximal and distal ends and defining a second lumen having an inlet and an outlet, said outlet being near said distal end;

means for introducing liquid through said inlet into said second lumen while said catheter is positioned within a patient; and means adjacent to said proximal end for providing pressurized fluid to said first lumen for compressing said second lumen for forcing said liquid towards and out of said outlet.

2. The catheter of claim 1, wherein said first wall is configured for lying flat against said first tube when no liquid is present within said second lumen.

3. The catheter of claim 1, wherein said first wall is formed from an elastic material which lies substantially flat against said first tube when no liquid is present within said second lumen.

4. The catheter of claim 1, wherein said outlet includes means for atomizing said liquid upon exit of said liquid from said second lumen.

5. The catheter of claim 4, wherein said atomizing means includes a portion of said outlet having a diameter larger than a diameter of said second lumen, for causing said liquid to disperse upon said exit.

6. The catheter of claim 4, wherein said atomizing means includes a plurality of attachment points of said first wall to said first tube at said outlet.

7. An endotracheal tube, comprising:

a proximal end;

a distal end;

a central body having a first wall defining a first lumen; and a second wall attached to said first wall within said first lumen, forming a second lumen between said first and second walls, said second wall being formed from a distensible, elastic material;

wherein said first wall includes an opening connected to said second lumen for introduction of medications therethrough into said second lumen, and wherein said second wall has a first side forming at least a portion of said first lumen and a second side forming at least a portion of said second lumen, such that pressure within said first lumen is transmitted through said second wall to said second lumen for propelling said medication towards said distal end.

8. The tube of claim 7, further comprising:

a third lumen within said wall;

a balloon carried at said distal end and connected to said third lumen; and means, connected to said third lumen, for inflating said balloon.

9. The tube of claim 7, further comprising a y-shaped port connected to said opening and having a first tip and a second tip, said first tip being adapted to receive a conventional syringe and said second tip being enclosed by a soft material for puncturing by a needle, said port for receiving said medications therethrough for introduction into said second lumen.

10. The catheter of claim 7, wherein said second wall is configured for lying flat against said first wall when no medication is present within said second lumen and when fluid is present within said first lumen.

11. The catheter of claim 7, wherein said second wall is configured to lie substantially flat against said first wall when no medication is present within said second lumen.

12. The catheter of claim 7, wherein said outlet includes means for atomizing said medication upon exit of said medication from said second lumen.

13. The catheter of claim 12, wherein said atomizing means includes a portion of said outlet having a diameter larger than a diameter of said second lumen, for dispersing said medication upon said exit.

14. The catheter of claim 12, wherein said atomizing means includes a plurality of attachment points of said second wall to said first wall at said outlet.

15. The catheter of claim 3, wherein the elasticity of said first wall is selected such that liquid within said second lumen causes said first wall to distend, and such that said elasticity tends to contract said first wall, thereby forcing said liquid distally.

* * * * *